United States Patent [19]

Dalla-Favera et al.

[11] Patent Number: 5,223,417

[45] Date of Patent: Jun. 29, 1993

[54] METHOD FOR TRANSFORMING HUMAN B LYMPHOCYTES

[75] Inventors: Riccardo Dalla-Favera; Stephanie Seremetis, both of New York, N.Y.

[73] Assignee: New York University, New York, N.Y.

[21] Appl. No.: 790,149

[22] Filed: Nov. 8, 1991

Related U.S. Application Data

[63] Continuation of Ser. No. 340,939, Apr. 20, 1989, which is a continuation-in-part of Ser. No. 41,803, Apr. 23, 1987, Pat. No. 4,997,764, and a continuation-in-part of Ser. No. 286,680, Dec. 19, 1988, abandoned.

[51] Int. Cl.$^5$ ............... C12N 15/01; C12N 15/02
[52] U.S. Cl. ............... 435/172.2; 435/69.6; 435/70.21; 435/172.3; 435/240.27; 530/388.1; 530/808; 530/809; 935/93; 935/100
[58] Field of Search ............ 435/172.1, 240.27, 172.2; 530/387

[56] References Cited

U.S. PATENT DOCUMENTS 4,652,522  3/1987  Kennett ........................ 435/68
4,804,627  2/1989  Hämmerling ................. 435/240.21

OTHER PUBLICATIONS

Stites, et al. (eds), 1990. Basic and Clinical Immunol. pp. 34-40.
*Cancer Cells*, 1984. G. F. Van Woude (editor). Cold Spring Harbor, New York, "Oncogenes . . . ".
Immunology Today. Mar. 1983. "Immortality by Transfection."
*Monoclonal Antibodies: Principles and Practice.* 1986. Academic Press, N.Y. J. W. Goding (ed).
Science News, vol. 123(8): 125. "Alternative in Antibody Production". Feb. 1983.
Genetic Eng. News May/Jun. 1983, p. 7. J. Cavagnaro.
PNAS 78(2):1181-4. T. G. Krontiris. 1981. "Transforming Activity of Human Tumor DNAs".
Science 208: 1033-5. 1980. K. Mercola et al. "Insertion of a new gene . . . ".
Biotec. Newswatch 3(4):1-2, "Genetic Eng. gets Toehold . . . " Feb. 1983.
Nunez, G., et al., *Proc. Natl. Acad. Sci.* USA 86:4589-4593, 1989.
Lombardi, L. et al., *Cell* "Pathogenesis of Burkitt Lymphoma", 49:161-170, 1987.
Z. L. Jonak, *Advanced Drug Delivery Reviews,* "Gene Transfection and Lymphocyte Immortalisation", 2:207-228, 1988.
L. Rothstein, *Blood,* "Amphotrophic Retrovirus Vector Transfer", 65:744-752, 1986.
C. J. Marshall, *J. Cell. Sci. Suppl.,* "The ras oncogenes", 10: 157-169, 1988.
R. Dalla-Favera, *Science,* "Transformation and plasmacytoid differentiation of human B lymphoblasts", 243:660-663, 1989. (Seremetis, et al.).

*Primary Examiner*—Christine M. Nucker
*Assistant Examiner*—T. Cunningham
*Attorney, Agent, or Firm*—Darby & Darby

[57] ABSTRACT

Disclosed herein is a method for transforming human B-cells preferably by infecting them with Epstein-Barr virus followed by transforming the Epstein Barr virus infected cells with an activated human ras gene. The transformed cells are useful for producing human monoclonal antibodies either without further manipulation or after fusion with antibody-secreting cells.

12 Claims, 3 Drawing Sheets

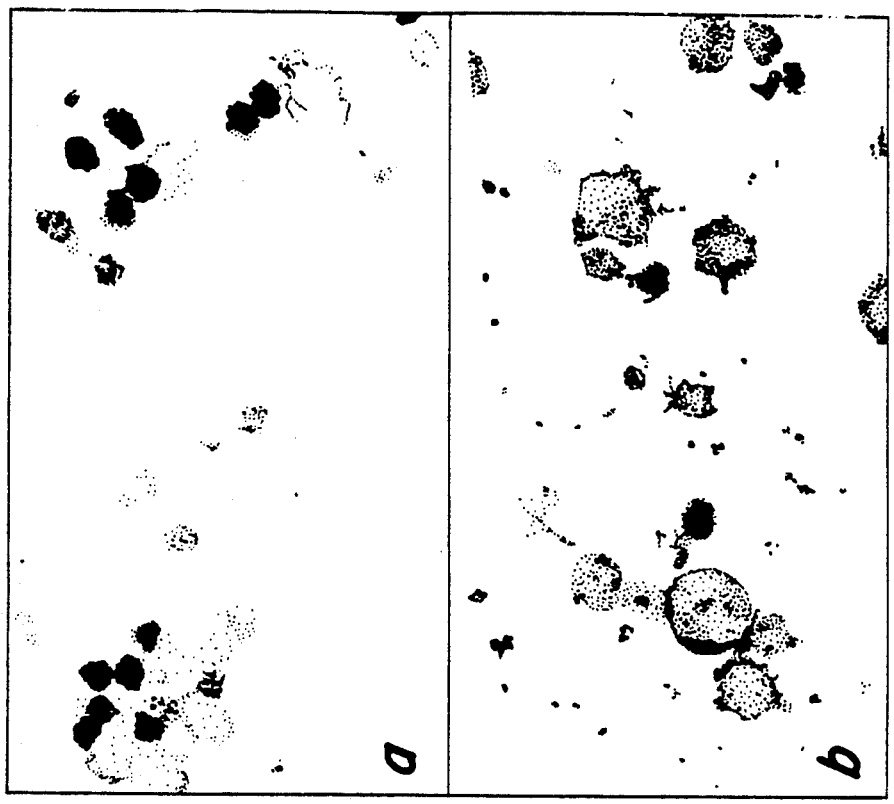
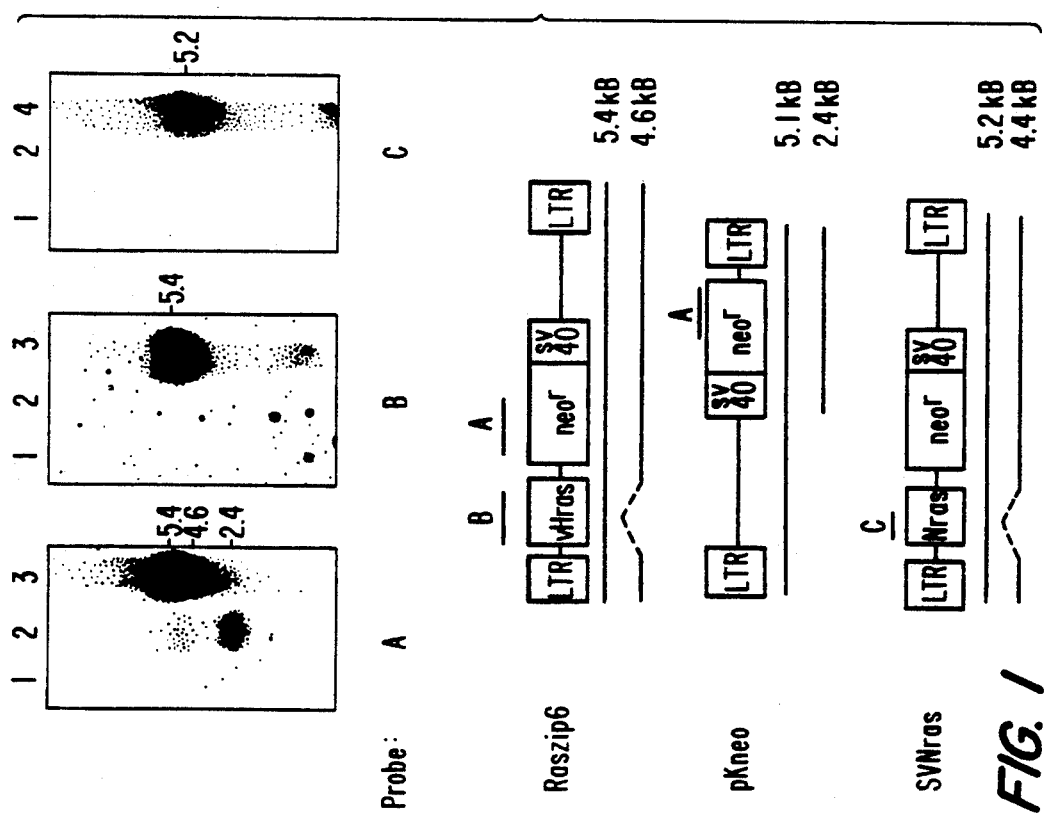

METHOD FOR TRANSFORMING HUMAN B LYMPHOCYTES

This is a continuation of application Ser. No. 340,939, filed Apr. 20, 1989 which is a continuation-in-part of copending application Ser. No. 041,803 (allowed), filed Apr. 23, 1987 of Riccardo Dalla-Favera and copending application Ser. No. 286,680 of Riccardo Dalla-Favera and Stephanie Seremetis filed Dec. 19, 1988. The entire disclosures of said applications are incorporated herein by reference.

FIELD OF THE INVENTION

This invention relates to a method for the production of transformed human cells that produce, or can be used to produce, human monoclonal antibodies and can also be employed to transform any mammalian cell.

BACKGROUND OF THE INVENTION

Since its introduction in 1975, the well-known Kohler and Milstein technique (*Nature* 256:495, 1975) for the production of mouse hybridoma cells has made it possible to produce large quantities of mouse antigen-specific monoclonal antibodies that are useful in a number of investigative, diagnostic and therapeutic applications. The mouse hybridoma cells, which are initially produced by the fusion of antibody-producing cells (B-lymphocyte cells, hereinafter referred to as B-cells) with malignant, transformed B-cells (in vivo transformed, myeloma cells from mice afflicted with myeloma or plasmacytoma) are capable of producing large quantities of monoclonal antibodies with predetermined specificities.

Using the Kohler and Milstein technique, a B-cell and a plasmacytoma cell are fused using, for instance, polyethylene glycol, lysolecithin or Sendai virus as the cell-fusing agents. A selectable marker must be present in the fused cells to enable them to be selected from parent cells and other non-hybridoma cells. As an example, the plasmacytoma fusion partner is generally deficient in an enzyme, (for instance, hypoxanthine-guanosyl phosphoribotransferase (HGPRT)) that is necessary for growth of the fused cell in certain media (hypoxanthine-, aminoprotein-, and thymidine- containing medium or HAT medium). This enzyme deficiency enables the resultant hybrids to be selected for their ability to grow in such media. This insures that only B-cell:plasmacytoma cell hybrids are recovered since neither parental cells (nor hybrids comprising B-cell: B-cell and plasmacytoma: plasmacytoma cell) can survive in selective media.

Murine antibodies produced with the Kohler and Milstein technique are generally unsuitable for administration to human subjects as in-vivo therapeutic agents, e.g., to provide passive immunity to an infectious agent. The extension of the Kohler and Milstein hybridoma technology to the production of human monoclonal antibodies has been limited, largely due to: (1) the lack of good human plasmacytoma cells for use as fusion partners; (2) the low frequency of cell fusion events ("fusion efficiency"); and (3) the relative scarcity of B-cells circulating in human blood and producing specific antibodies against antigens of interest (and the inherent difficulties in isolating such cells). These factors make it difficult to obtain hybridoma cell lines secreting human monoclonal antibodies of a predetermined specificity.

Casali et al. (*Science* 234:476–479, 1986) disclosed a method which represents some progress toward making human monoclonal antibody-producing cells. Normal B-cells obtained from peripheral human blood were pre-selected for their specificity to a given antigen using Fluorescence-Activated Cell Sorting (FACS). Positively selected clones were then established as lymphoblastoid cells in vitro by infecting such cells with Epstein-Barr virus (EBV). The EBV infected cells produced antigen-specific human monoclonal antibodies. However, the method of Casali et al. has several significant drawbacks which impair its usefulness: (1) the amount of monoclonal antibodies produced by the Casali et al. cells is relatively low, and (2) the antibody producing cells are relatively unstable and some clones stop antibody production prematurely. In addition maintenance of the antigen-specific antibody production requires repeated cloning of the cells, a time-consuming and inefficient procedure given the low clonogenic (i.e. growth) properties of the resultant lymphoblastoid or lymphoblastoid cell lines (LCL); (3) large-scale production and purification of the monoclonal antibodies is inefficient in view of the long doubling time and high serum requirements of the LCL; and (4) the LCL produced by this process cannot be grown as tumors in animals. Such tumor cell growth permits the amplification and purification of antibodies from ascitic fluids, an efficient method for large scale antibody production that is widely used in making murine monoclonal antibodies. Finally, the Casali et al. method does not dispense with the requirement for identifying a human B-cell specific to a certain antigen.

Copending U.S. patent application Ser. No. 041,803 (allowed) filed Apr. 23, 1987 of Riccardo Dalla-Favera discloses a method for the production of human monoclonal antibody-producing cells. Specific B lymphocytes are selected using the method of Casali et al. (supra), infected with Epstein Barr virus (EBV) and transfected with activated c-myc DNA sequences. The resultant cells are tumorigenic (i.e. can grow in semisolid medium and animals such as rats or mice) and clonogenic and produce monoclonal antibodies of a predetermined specificity. However, it was found that these cells still produce relatively low amounts of antibody because the transfected lymphoblastoid cells had not undergone differentiation.

Currently there is no convenient and reliable system available for the production of human monoclonal antibodies wherein the monoclonal antibody-producing cells are stable, highly malignant and which can be readily manipulated to produce high antibody titers.

It, is therefore an object of the present invention to provide a method for the production of tumorigenic human cells that are capable of producing human monoclonal antibodies.

A further object of the present invention is to provide a transformed lymphoblastoid cell that is useful as a fusion partner in the production of human monoclonal antibodies.

Another object of the present invention is to provide a transformed lymphoblastoid cell that demonstrates high level proliferative, differentiation and antibody production properties.

Another object of the present invention is to produce a new human cell line comprising human B-cells infected with Epstein-Barr virus and which have at least one exogenous activated K-, N- or H-ras oncogene DNA sequences.

SUMMARY OF THE INVENTION

The present invention provides a method and a cell line for producing human monoclonal antibodies. According to one embodiment, human B-cells that produce an antibody directed against a specific antigen may be isolated. The isolated human B-cells are immortalized and transformed (transformation is the process of introducing DNA into cells) with an activated oncogene (preferably using an appropriate vector). The immortalized human B-cells comprise malignant transformants which undergo terminal differentiation into plasma cells. These clonogenic, tumorigenic cells are effective for producing large amounts of human monoclonal antibodies.

In one particular aspect, the present invention provides a method for preparing human monoclonal antibody producing cells that can grow in culture comprising the steps of infecting human B-cells producing antibodies of a desired specificity with Epstein-Barr virus, and transforming said Epstein-Barr virus infected human B-cells with a vector containing an activated ras gene.

In another embodiment, the present invention provides a method for obtaining transformed human B-cells comprising the steps of infecting human B-lymphocytes with Epstein-Barr Virus, recovering the Epstein-Barr virus-infected human B-lymphocytes, transforming the virus-infected B-lymphocytes with an activated ras vector, and recovering the transformed human B-lymphocytes. The thus transformed cells can be used as fusion partners in cell-fusions with untransformed human B-cells that have been sensitized with an antigen to produce an antibody with the desired specificity.

In a further aspect, the present invention provides a transformed human cell comprising a human B-lymphocyte infected with Epstein Barr virus, said cell containing DNA segments coding for a selectable genetic marker, and an activated ras gene in the proper orientation and correct reading frame.

These and other aspects of the present invention will be apparent to those of ordinary skill in the art in light of the present description, accompanying claims and appended drawings.

BRIEF DESCRIPTION OF THE DRAWINGS

FIG. 1 is a Northern Blot analysis of ras production by cells infected with the retroviral vectors of the present invention and also contains schematic representations of the probes used in said Blot.

FIG. 4 is an autoradiograph showing thymidine incorporation in cells expressing ras oncogenes.

DETAILED DESCRIPTION OF THE INVENTION

Figure 2:
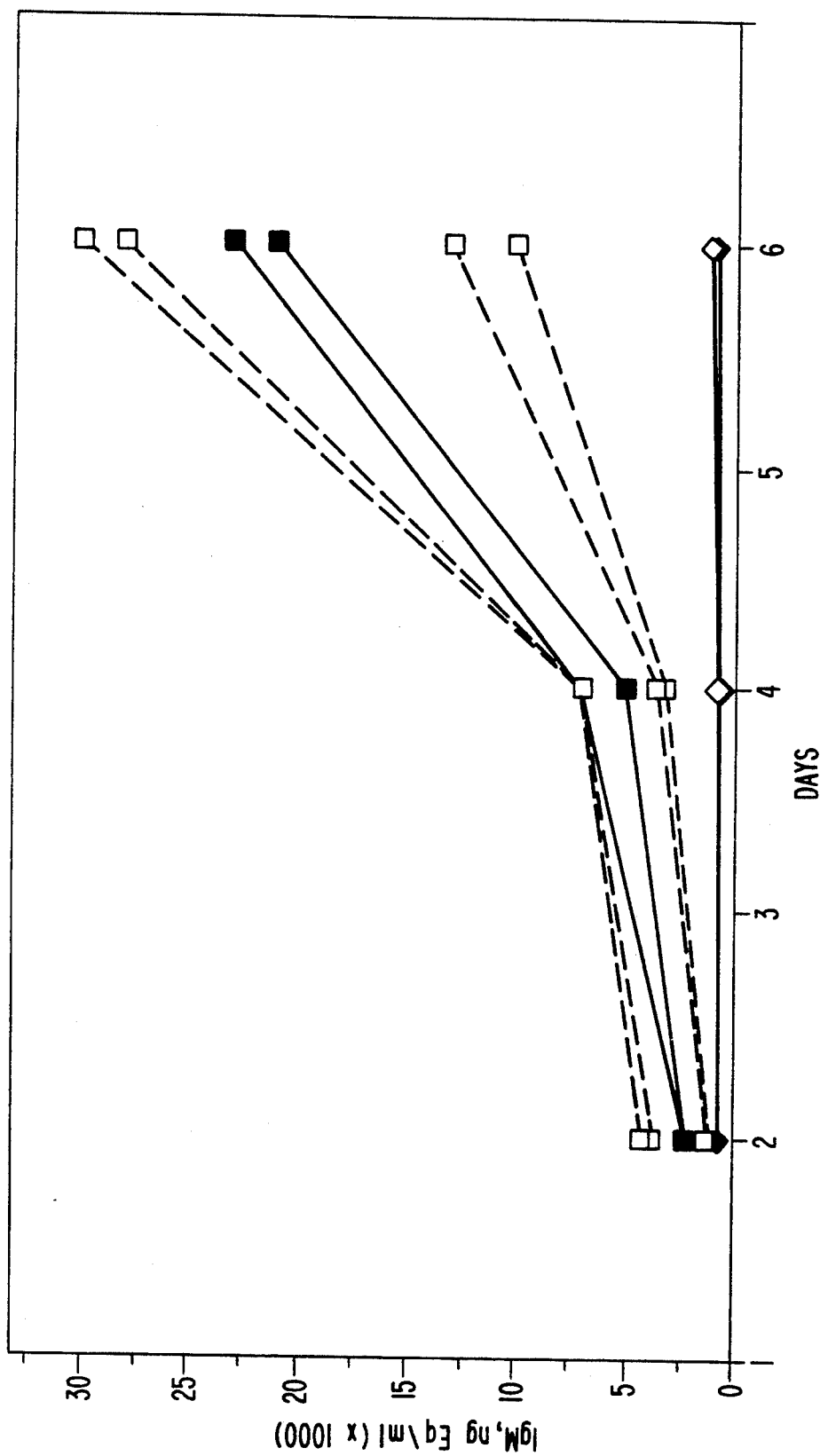
FIG. 2 is a graph showing the kinetics of antibody production of a B-cell transformed by the method of the present invention.

All literature and patent applications cited in the specification are hereby incorporated by reference in their entirety.

This invention involves a method for producing transformed human cells. The method is particularly useful for transforming normal human B-cells into malignant, transformed, differentiated, monoclonal antibody-producing cells. This is important and unexpected as heretofore it was not believed to be possible to make viable, human, transformed, fully differentiated B-cells using in vitro manipulations.

Whereas conventional hybridoma cells are the product of a fusion event using a transformed lymphoblastoid cell and a normal B-cell, the method of the present invention, in one aspect, requires only genetic manipulation of a normal human B-cell. Using the method of the invention, transformed human B-cells, capable of producing human monoclonal antibodies of any desired specificity, can be readily and easily obtained.

In one aspect, the method of the present invention involves selecting a human B-cell producing antibodies to a specific antigen which may be predetermined. The selected B-cells are then infected with Epstein-Barr virus (EBV). The EBV-infected B-cells are then treated so that they take up and express an activated ras oncogene (e.g. H-, N- or K- ras oncogenes). The result is a relatively high incidence of cells producing specific monoclonal antibodies and capable of being grown in vitro in semi-solid media or in vivo in animals.

Thus, the process described above is used to produce human transformed B-cells secreting antibody of predetermined antigenic specificity.

In an alternative embodiment, B-cells are isolated from a patient known to produce antibodies directed against a specific antigen. The B-cells are immortalized with EBV and transformed in bulk with an activated ras gene. Specific immortalized, ras transformed monoclonal antibody producing cells are then identified and isolated using the method of Casali et al., supra.

Using either of the above embodiments, the frequency of obtaining the desired EBV-infected, ras transformed LCL is greatly increased over that obtainable by cell fusion using the traditional Kohler and Milstein (supra) technique. The efficiency of transformation using the method of the present invention is approximately $1 \times 10^{-1}$ to $1 \times 10^{-2}$ (i.e., 1–10%), whereas the efficiency of the Kohler and Milstein technique is approximately $1 \times 10^{-6}$ (i.e. 0.0001%). Thus, the method of the present invention provides an improvement in efficiency comprising several orders of magnitude.

In another embodiment the infection-transformation process described above can be applied to human B-cells which had not been pre-selected for the production of specific antibodies (but which nonetheless have the requisite biochemical machinery in place and produce and secretic antibodies). After infection and ras transformation, such B-cells will possess all of the properties of transformed B-cells, i.e. the ability to overexpress ras (or the mutations discussed below), the ability to grow in semi-solid media and in animals as well as the ability to secrete antibody. However, such infected/transformed B-cells can be used as fusion partners together with specific antibody-secreting B-cells to produce hybridomas using more conventional techniques (such as the well-known Kohler and Milstein technique cited above or other hybridoma technology). Such a cell line, designated CB 33 ras II, has been deposited with the American Type Culture Collection (ATCC, Rockville, Md.) under Accession No. ATCC CRL 10011.

However, for use as a fusion partner, the immortalized, ras transformed B-cell is preferably first selected for an enzyme deficiency (using techniques well-known in the art) such as the HGPRT mentioned above. As in the above-mentioned mouse plasmacytoma cell used in the Kohler and Milstein technique, this allows for the selection of monoclonal antibody producing hybridomas by their ability to grow in HAT medium.

Specific monoclonal antibodies produced by the hybridomas of the present invention can be recovered from the supernatants of antibody-producing cells and purified using techniques well-known in the art such as ammonium sulfate precipitation, Protein-A Sepharose chromatography, High Performance Liquid Chromatography (HPLC), and/or combinations thereof.

EBV-infected B-cells demonstrate properties which are intermediate between normal human cells and malignant tumorigenic human cells. The EBV infected B-cells (LCL) exhibit the ability to grow in tissue culture indefinitely in the presence of serum-containing medium. However, they lack the ability to produce colonies when grown in semi-solid medium (agar) and are unable to grow when injected into susceptible hosts, such as mice or rats. Therefore, the method of the present invention comprises transforming immortalized (e.g. EBV-infected) human B-cells with a vector which confers upon the recipient cells the ability to differentiate (i.e. to acquire the properties of differentiated B-cells) and preferably also one or more of the following properties: (a) the ability to grow in semi-solid media, or animals and (b) the ability to express high levels of certain gene products. A vector that contains an activated ras gene is capable of conferring all of these properties to the target cell (hereinafter an "activated ras vector").

The conversion of normal mammalian cells to the transformed state is usually associated with the activation of one or more oncogenes. For example, the H- ras gene is that portion of the genome of the Harvey Sarcoma Virus that is responsible for the ability of the virus to induce a variety of tumors within weeks after injection of the virus into newly hatched chicks. Thus, a cell can become transformed by a virus by acquiring the viral oncogene, such as K-ras. A cell can also be transformed through overexpression of an apparently normal gene such as N-ras, resulting in higher observed concentrations of the expression products of the gene (and any genes that are co-expressed with the normal gene) or through mutation (see below). The ras gene has been found to be activated in some cases of multiple myeloma and in many other human malignancies. Ras genes have been identified in mammals, birds, insects, mollusks, plants, fungi and yeasts.

Ras genes, independent of their species of origin, code for proteins that are associated with the plasma membrane, bind guanine nucleotides, and have GTPase (guanosine triphosphatase) activity. It is believed that ras proteins may participate in the transduction of signals across cellular membranes. Although an activated ras gene is preferred for use in the present invention, any activated oncogene (or other gene) which can cause immortalized B-cells to differentiate into mature plasma cells may be employed.

In other words, a gene that causes the immortalized B-cells to differentiate into mature plasma cells (while preserving their ability—if such B-cells already process such ability—to secrete antibody) would be useful in the process of the present invention. Naturally, a gene (as in the case of the ras oncogene) that also confers on the transformed antibody-secreting cell (or to a hybridoma made with a cell that has been transformed in accordance with the present invention) at least one of the following properties is preferred: (1) the ability to grow in animals, (2) the ability to grow in semi-solid media and/or (3) the ability to express large quantities of antibody.

The EBV-infected/ras-transformed cells of the present invention produce monoclonal antibodies, display a relatively short doubling time (on the order of about 36 hours), are clonogenic in semi-solid media and are tumorigenic in experimental animals. In vitro transformation (i.e. generation of clonogenic and tumorigenic cells) of human B-lymphocytes by an activated ras gene has not been previously carried out.

Normal human B-cells for use in the present invention can be isolated from peripheral human blood using conventional methods that are well known to those in the art. The isolated B-cells can be selected for their ability to produce antibodies directed against any antigen using the method of Casali et al., supra as described in Example 5 below (or not so selected—as will be described below by reference to an alternative embodiment). Once human B-cells that produce antibodies directed against a specific antigen have been isolated, they are infected with EBV (obtained by culturing EBV-infected marmoset leukocyte cell line B95-8, available from the American Type Culture Collection (ATCC Rockville, MD) as ATCC CRL 1612), according to well-known methods as illustrated in Example 2 below. The amount of EBV needed for infection is the quantity that will result in a successful infection or, about one transforming unit per cell as described below.

In a particularly preferred embodiment, prior to EBV infection the specific antibody-producing human B-cells (that have been obtained from the peripheral blood) are screened. The mature B-cells that produce IgG are identified and segregated. The IgG producing B-cells yield antibodies having a higher affinity for specific antigens. The isolated IgG producing B-cells are preferred for use in practicing the method of the invention.

Most EBV-infected B-cells that have been studied, have been found to produce IgM. However, IgG producing B-cells can be easily selected because they display differentiation-associated surface markers such as PCA-1, B-1 (commercially available antibodies to these markers can be obtained from Coulter Immunology, Hilleah, Fla.) and OKT10 (commercially available antibodies to OKT10 can be obtained from Ortho Diagnostics) which can be selectively identified as shown in Example 4 below.

After the B-cells have been immortalized, an effective amount of an activated ras gene is introduced into these LCL as discussed below. An effective amount of an activated ras gene is the quantity or titer that accomplishes at least the first of the following three goals (a) differentiation of the B-cells; (b) transformation of the B-cells into the "malignant" phenotype; and (c) production by the B-cell of high levels of ras expression products (and products of co-expressed genes). An activated ras gene is defined as a ras gene (e.g. H-, N- or K-ras) which expresses a mutated gene product or a constitutive (i.e., not regulated) high level of the normal (non-mutated) ras protein. High levels of the normal protein or certain mutations in the coding region (see below) of this protein have been found to induce unrestrained cell division in human cells. For purposes of the invention the ras gene may be "activated" by:

(1) mutation of "restraining" sequences present in the gene; or (2) insertion of "enhancer" elements adjacent to said gene; or (3) by a combination of these two procedures.

Any technique for introducing DNA into eukaryotic cells can be used for transformation of the vector materials into mammalian cells. Well-known techniques for introducing DNA into mammalian cells which can be used in practicing the present invention include, but are not limited to, retroviral vectors, microinjection, calcium phosphate precipitation, DEAE-dextran protoplast fusion or electroporation. Retroviral vectors are preferred because of the high efficiency (approaching 10%) of gene transfer. Other techniques may be more efficient when using different cell types as is well known in the art. The most efficient technique for use with a given cell type can be determined by routine experimentation.

Microinjection involves the direct injection of vectors into the nucleus of eukaryotic cells (as described in Capecchi, M. R., *Cell* 22:479-488, 1980). A drawback of this technique is that it requires sophisticated machinery for the delivery of very small volumes (nanoliters) and an operator with considerable technical expertise.

DEAE-dextran-mediated protoplast fusion employs a fusion event between the recipient cell and a bacterium carrying the vector of interest (Sandri-Goldin, R. M. et al *Mol. Cell Biol.* 1:743-752, 1981).

Calcium-phosphate precipitation induces uptake of DNA (or vector) into cells (Graham, F. L. et al, *Virology* 52:456-467, 1973) The vector is then translocated into the nucleus of these cells.

Electroporation involves exposing a cell suspension to a brief electrical impulse which results in the transfer of DNA into cells (Potter, H. L. et al., *Proc. Nat. Acad. Sci.*, USA 81:7161-7165, 1984). DNA entry is believed to occur via local areas of reversible membrane breakdown (or pores) created by the external electrical field.

The activated ras vectors used in the Examples presented below, termed SVNras and raszip6, are produced by standard cloning techniques, well-known in the art, as described in Example 3 below. Retroviral vectors are preferred because of their high gene transfer efficiency. The use of the raszip6 vector is particularly preferred for use in the present invention because this retroviral vector is available in a high viral titer, therefore allowing for a more efficient gene transfer. Although specific examples of vectors useful in practicing the invention are presented herein, it will be apparent to those skilled in the art that many different constructs can be employed, provided that they confer to the transformed (previously immortalized) cell the ability to fully differentiate and preferably also the abilities to grow in semisolid media and to produce a high level of the normal protein or a mutated gene product.

To be useful in practicing the present invention a vector must meet the following minimum requirements:
(1) contain an activated ras gene (or another gene as described above); and (2) be capable of constitutive (i.e. non-regulated) expression in human cells.

In addition, incorporation of a selectable genetic marker in the retroviral vector is preferred for practicing the invention. This permits efficient selection of the EBV-infected, successfully ras-transformed cells. In this selection process, only EBV-ras cells are able to grow while all other cells (e.g., non-transformed EBV-infected B-lymphoblastoid cells) are killed. Selectable genetic markers that can be used in the vectors of the present invention include, by way of non-limiting example, resistance to an antibiotic substance, e.g., neomycin, antibiotic G418 (a variant of neomycin), or hygromycin, or resistance to any other substance that confers a selective advantage to the transfected cells. Indeed, any selectable genetic marker which can be expressed in mammalian cells can be used in practicing the invention. Human lymphoblastoid cells can be made G418 resistant by incorporation of a gene which inhibits the activity of this antibiotic.

Although specific retroviral vectors for use in practicing the present invention are disclosed herein, practice of the invention is not limited to these vectors. Among the other vectors which may be used in practicing the invention are plasmid vectors with the desired properties described above capable of integration into the host cell genome (such plasmids may be constructed in accordance with techniques that are well-known in the art), or other retroviral vectors (as described in Cepko et al. *Cell* 37; 1053 (1985)).

The activated human ras gene used in the examples of the present invention was isolated from Harvey Sarcoma virus and is available from the ATCC (Accession No. 41013, American Type Culture Correction, Rockville, Md.) However, any activated ras gene may be used. Three ras genes have already been identified in the mammalian genome. These are designated H-ras-1, K-ras-2, and N-ras (as described in Barbacid, M. *Ann. Rev. Biochem.* 56: 779-827, 1987). The vectors that are useful in practicing the instant invention should have the ability to produce the mutated gene product discussed above and/or high levels of the normal ras gene product required for the transformation of the EBV-infected B-cells into fully differentiated, tumorigenic B-cells. Activation of the ras gene can be accomplished by (i) the mutation of a specific sequence DNA of the gene, leading to the production of an abnormal protein and/or (ii) by the insertion of an exogenous "enhancer" sequence in the vector DNA adjacent to the ras gene leading to the overproduction of a normal protein. Enhancer sequences have been isolated from the genome of certain tumor viruses (such as Simian Virus 40 (SV40), Banerji et al., *Cell* 27:299, 1981), and retroviruses (Llucin et al *Cell* 33:705, 1983), among others and from the genome of normal mammalian cells (such as the immunoglobulin gene enhancers, as described in Church et al., *Nature* 313:798, 1985). These sequences have been found to increase the expression of adjacent genes, and their presence in the ras vectors of the present invention leads to deregulated expression. The presence of glycine at position 12 of the ras protein appears to be necessary for the regulated expression of the ras protein. Substitution of $Gly^{12}$ by any other amino acid residue (with the exception of proline) results in the oncogenic activation of these molecules. In addition, mutations at codon 13, 59 or 61 (and others) will also result in oncogenic activation (as described in Barbacid, M., *Ann. Rev. Biochem.* 56: 779-827, 1987). The deregulated and/or mutated ras gene is termed "activated". Any method suitable for the activation of the human ras gene can be used in practicing the methods of the present invention.

The present invention is further described below in specific examples which are intended to illustrate the invention without limiting its scope.

EXAMPLE 1: ISOLATION OF B-CELLS

The method below has been used for the initial B-cell selection from blood or appropriate blood fractions.

Blood obtained from healthy males and females was placed on a gradient medium for separating lymphocytes (Pharmacia, Piscataway, N.J.). Monocytes were removed from other mononuclear cells by two cycles of incubation at 37° C. in plastic 150 cm² tissue culture flasks. The mononuclear fraction was incubated on ice with sheep red blood cells (SRBC) treated with AET (2-aminoethylisothioronium bromide hydrobromide) (Sigma, St. Louis, Mo.) to allow for rosette formation. Non-erythrocyte rosette-forming cells (i.e. non-T-cells) were recovered after application of the whole SRBC mononuclear fraction to a lymphocyte-separating medium gradient. The nonadherent, non-rosetting fraction was constituted of at least 50% B-cells, less than 1% monocytes and variable amounts of other lymphocytes.

EXAMPLE 2: EBV INFECTION OF CB33 CELLS

EBV was obtained from culture fluids of B95-8 marmoset lymphoma cells (ATCC No. CRL 1612) incubated in the presence of $1.62 \times 10^{-8}$M 4-phorbol-12 beta-myristate-13-alpha-acetate (TPA, Sigma Fine Chemical Company, St. Louis, Mo.). The virus preparation had a titer of $5 \times 10^5$ transforming units per ml, one unit being the minimum amount of virus-transforming $10^4$ purified human B-cells. Lymphocytes, at $1 \times 10^6$ per ml were exposed to the EBV-containing medium from B85-9 cells, at a multiplicity of infection of 1 transforming unit per cell.

The EBV-infected cells were then cultured for 3-4 weeks in culture medium (RPMI 1640, GIBCO, Grand Island, N.Y.) continuing 10% fetal calf serum to allow the virus to immortalize these cells.

EXAMPLE 3: CONSTRUCTION OF THE VECTORS OF THE PRESENT INVENTION

The retroviral vectors used in the present invention, SVNras and raszip6, were constructed as follows.

SVNras (described in Souyri et al., *Virology* 158: 69-78, 1987) was derived from the vector SVX (constructed as described in Capeko et al., *Cell* 37: 1053-1062, 1984). The SVNras vector consists of the following elements between the long terminal repeats (LTR) of Maloney murine leukemia virus (the sequence of which is described in Hoffmann et al., *J. Virol.* 44: 144-153, 1982) the region necessary for viral packaging, the 5' and 3' splicing signals, a DNA sequence coding for neomycin resistance, origins of replication of SV40 virus and the plasmid pBR322 and an activated N-ras gene. The activated N-ras gene was inserted into a unique BamHI site in SVX in place of missing retroviral gag-pol sequences.

Raszip6 was constructed by inserting the viral H-ras gene (map positions 4,000 to 4,710, Dhar et al., *Science* 217: 934-937) into the BamHI site of SVX (Capko et al., supra). The biological properties of raszip6 have been described (Dotto et al., *Nature* 318: 472-475, 1985).

EXAMPLE 4: BIOLOGICAL EFFECTS OF ACTIVATED RAS GENES

In the example presented below the biological effects of activated H-ras and N-ras oncogenes in the same target cells were examined. These oncogenes induced malignant transformation in LCL and, in addition, lead to dramatic phenotypic changes involving terminal differentiation of lymphoblasts into plasma cells.

An activated H-ras allele derived from Harvey Sarcoma Virus (as described in Dhar, R. et al., *Science* 817:934, 1982), or a human N-ras allele, activated by a mutation at codon 12 (as described in Souyri et al., *Virology* 158:69, 1987), were introduced into LCL derived from normal cord blood (CB33 line) or from adult peripheral blood (UH3 line) by use of amphotropic retroviral vectors containing the G418-resistance (neo) gene as a selectable marker (see above and FIG. 1). A vector (pKneo) containing only the G418 resistance gene was used as a control. After infection, cells were selected in bulk for antibiotic resistance or, in order to ensure the selection of independently infected clones, were plated in limiting dilution followed by antibiotic selection of individual clones. Using either protocol, cell lines were established 2-3 weeks after infection and the presence of clonally distinct viral integration sites was confirmed by Southern blot analysis (not shown).

The expression of retrovirus-encoded genes in infected LCL was examined. The results are shown in FIG. 1. RNA was extracted from CB33 cells (Lanes 1), pKneo-infected CB33 cells (Lanes 2), raszip6-infected CB33 cells (Lanes 3), and SVNras infected CB33 cells (Lane 4) purified by the well-known guanidine isothiocyanate method, electrophoresed in 0.9% agarose-2.2 M formaldehyde gels, transferred to nitrocellulose filters, and hybridized with the indicated probes. Schematic representation of the retroviral vectors probes used and expected hybridizing transcripts are also shown in FIG. 1. Northern blot hybridization analysis showed the presence of viral ras genes within the genomic-size viral transcripts (FIG. 1).

Evidence of phenotypic changes in all cell populations carrying either H- or N-ras oncogenes was immediately manifested as increased cellular volume and increased tendency to adhere to plastic. Morphological examination by light microscopy of cells prepared by routine Giemsa cytochemical staining, well-known in the art, revealed that both parental and control infected CB33 and UH3 cells retained the typical morphology of EBV-immortalized lymphoblastoid cells (small cell volume, high nucleus-to-cytoplasm ratio, multiple prominent nucleoli). In contrast, a significant fraction (>80%) of cells carrying ras oncogenes showed morphological evidence for plasma cell differentiation including an increase in cytoplasm, eccentric placement of the nucleus with the appearance of a single prominent nucleolus and an increase in the number and size of cytoplasmic inclusions. The remaining cells displayed a relatively less mature, but still plasmacytoid phenotype (see below and FIG. 4). In FIG. 4, the mature plasmacytoid cells are the large lighter shade cells predominant in FIG. 4b. The less mature cells are the darker, smaller ones predominant in FIG. 4a.

Next, evidence was sought of plasma cell differentiation by analyzing immunoglobulin secretion and the expression of cell surface markers associated with terminal differentiation of B-cells to plasma cells (as described in Foon, K. A. and Todd III, R. F., *Blood* 68:1, 1986).

Cells were plated in triplicate at $2 \times 10^4$ well in a 96-well microtitre plate, supernatants were harvested at 2, 4, and 6 days, and assayed for the presence of IgM by an ELISA assay using alkaline-phosphatase-linked antibody to human IgM. No IgA or IgG secretion was detected in any of the infected cell lines (consistent with the fact that the parent lymphoblastoid cells were not selected for IgG secretion). The results are shown in FIG. 2 (the abscissa is days after plating).

In FIG. 2, diamonds refer to cell lines infected with the pKneo virus (control) and squares refer to cell lines infected with the raszip6 virus. Each curve represents data from cell lines derived from distinct infection events. Solid lines represent data from cell lines derived from infection and selection in bulk. Dashed lines represent data from cell lines which were the product of selection of clones.

In all cell populations carrying ras oncogenes there was a marked increase in the secretion of IgM, up to a maximum of a fifteen-fold increase over control infected cells (FIG. 2). This increase in IgM secretion was detectable in all oncogene expressing cells including both bulk and clonally infected cells. These cells produced between 10 micrograms and 100 micrograms of antibody per ml of culture fluid.

The cell surface expression of lineage-, differentiation-, and activation-specific antigens was studied using monoclonal antibodies in indirect immuno-fluorescence and flow cytometric analysis. The results are shown in FIG. 3.

Figure 3:
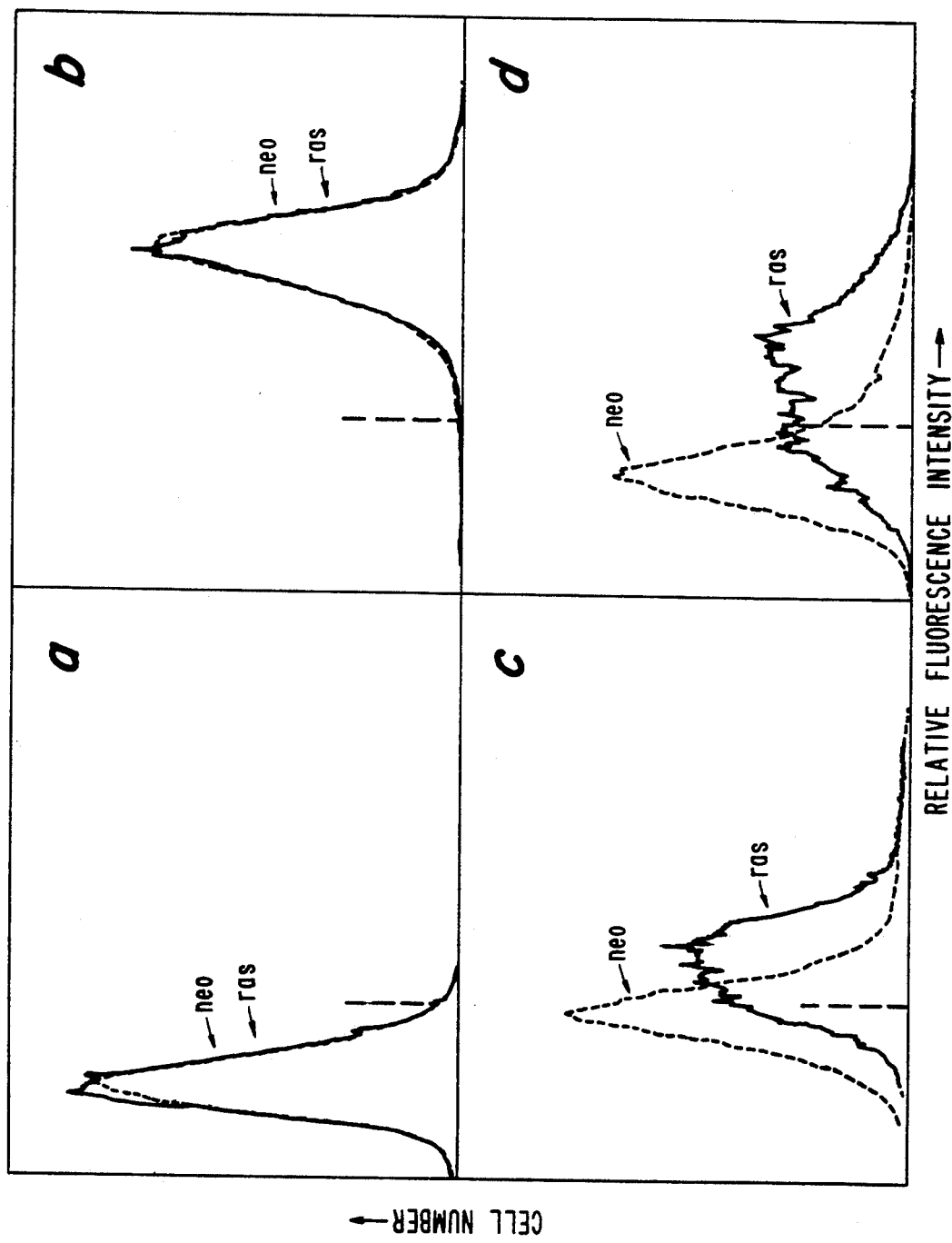
FIG. 3 is a series of graphs showing the increased expression of plasma cell specific antigens in cells transformed according to the method of the present invention.

In FIG. 3, pKneo-infected (dotted lines, neo) and raszip6-infected (solid lines, ras) CB33 LCL were labelled by indirect immunofluorescence and analyzed by cytofluorometry using the panel of monoclonal antibodies (MoAbs) described in Gotch, F. in *Leukocyte Typing III: White Cell Differentiation Antigens*, A. J. McMichael, Oxford Press, Oxford, 1987. Representative data were obtained using MoAb MOPC-21 (an isotype-identical negative control, panel a), MoAb TS-1-22 (used as a control with specificity for an antigen, LFA-1 [CD11a], whose expression is not changed, panel b), MoAb PCA-1 (panel c), and MoAb OKT10 (panel d). Analogous results were obtained when analyzing LCL expressing N-ras oncogenes.

Among many markers studied, the most significant and consistent changes were noted in the expression of the OKT10 (CD38) and PCA-1 antigens as manifested by both an increase in the percentage of antibody-reactive cells and increase of the antigen density in LCL expressing either H- or N-ras oncogenes (FIG. 3). Expression of both of these antigens is known to increase with plasma cell differentiation.

Ras oncogene expressing cells were then analyzed for growth properties associated with neoplastic transformation. First the ability of these cells to form colonies in soft agar was assayed. The results are shown in Table 1 below.

TABLE 1

IN VITRO CLONING EFFICIENCY AND IN VIVO TUMORIGENICITY OF LCL INFECTED WITH RETROVIRAL CONSTRUCTS

| CELL LINE | CLONING EFFICIENCY | TUMORIGENICITY tumors/injection | latency |
|---|---|---|---|
| BL (P3HR1)[x] | 24% | 4/4 | 2–3 wks. |
| CB-33pHEBOSVmyc2,3* | 2.20% | 4/6 | 3 wks. |
| CB33 | NA | 0/12 | NA |
| CB33 neo | 0 | 0/12 | NA |
| CB Hras II@ | 0.31% | 6/6 | 2–3 wks. |
| CB Hras III@ | 0.28% | 5/6 | 2–3 wks. |
| CB33 Hras IV.1# | 0.35% | 6/6 | 2–3 wks. |
| CB33 Hras IV.2# | 0.25% | 5/6 | 2–3 wks. |
| CB33 Hras I@ | 0.22% | NT | |
| UH3 | 0 | 0/6 | NA |
| UH3 neo | 0 | 0/6 | NA |
| UH3 Hras I@ | 0.07% | 5/6 | 2–3 wks. |
| UH3 Hras II@ | 0.09% | 4/6 | 2–3 wks. |

TABLE 1-continued

IN VITRO CLONING EFFICIENCY AND IN VIVO TUMORIGENICITY OF LCL INFECTED WITH RETROVIRAL CONSTRUCTS

| CELL LINE | CLONING EFFICIENCY | TUMORIGENICITY tumors/injection | latency |
|---|---|---|---|
| UH3 Nras I@ | 0.10% | 4/6 | 2–3 wks. |

NT = not tested
NA = not applicable
[x]Burkitt Lymphoma cell line used as a positive control.
*CB33 LCL transformed by a c-myc oncogene.
@LCL derived from infection and selection in bulk.
LCL clones derived from selection in limiting dilution.

As seen in Table 1 above, the expression of both H- and N-ras oncogenes appeared to confer a modest, yet consistently detectable clonogenic capability to both CB33 and UH3 LCL under conditions where no colonies were formed by parental or control infected lines. As a second assay for malignant phenotype, the ability of LCL expressing ras oncogenes and control LCL to form tumors in vivo when injected subcutaneously into a thymic nude mice was tested.

LCL expressing the mutated ras genes were tumorigenic, with subcutaneous tumors appearing 2–3 weeks after injection (Table 1). These results indicate that ras oncogenes can confer a rather weak, yet clearly and consistently identifiable transformed phenotype to LCL.

The relationship between proliferation and terminal differentiation in the LCL containing ras oncogenes was then investigated. Two scenarios could be envisioned. First, ras oncogenes could stimulate uncontrolled proliferation associated with stochastic (i.e. random) entrance into a terminal differentiation pathway, resulting in a heterogeneous population of cells including both self-renewing and terminally differentiating proliferatively quiescent subsets. Alternatively, ras oncogene expression could confer proliferative capacity to terminally differentiated cells, resulting in a phenotypically homogeneous population composed of mature, proliferating elements. To discriminate between these two possibilities DNA replication was studied at the single cell level by autoradiographic determination of [$^3$H]-thymidine uptake. The results are shown in FIG. 4. In FIG. 4, [$^3$H]-thymidine (1 uC/ml), was added to the growth medium of pKneo-infected (Panel a) and raszip6-infected (panel b) UH3 LCL which were then harvested at 24 hours and transferred to glass slides by cytocentrifugation. Slides were coated with NTB-2 emulsion (Eastman Kodak, Rochester, N.Y.), allowed to expose for 12 days at 4° C., developed, counterstained with Giemsa reagent and assessed for thymidine incorporation. Counting of 200 cells from this experiment showed 61% positive (5 granules/nucleus) cells in pKneo-infected UH3 LCL and 22% positive cells in raszip6-infected UH3 LCL. Analogous experiments performed in CB33 LCL showed 60% and 39% positive cells for pKneo-infected and raszip6-infected LCL respectively.

As shown in FIG. 4, cells expressing the ras oncogene displayed an heterogeneous pattern, with thymidine incorporation limited to the smaller, more immature elements and virtually no evidence of DNA replication in the more mature the first scenario described above, the possibility remained open that the observed heterogeneity was due to clonal variations of cells expressing different levels of ras oncogene. To directly address this issue, clonogenic cells, namely cells recovered from colonies in semi-solid medium (Table 1 above), were tested to determine whether they were restricted to self-renewal or whether they were also able to generate differentiated progeny. Upon replating in semi-solid medium, these cells did not show any increased clonogenic ability while they rapidly generated mature progeny when grown in liquid culture (not shown). Taken together, these results indicate that ras oncogene expression in LCL stimulated both self-renewal and stochastically determined entrance into a pathway leading to terminally differentiated, quiescent plasma cells.

The results presented above indicate that ras oncogenes can both stimulate sustained growth by cooperating with EBV in transforming LCL and trigger terminal differentiation which is normally blocked in EBV-infected B-cells. Differentiation appears to represent a specific effect of ras oncogene expression rather than a consequence of increased proliferation since expression of c-myc oncogenes in LCL caused analogous alterations of growth, yet no differentiation was observed (not shown).

EXAMPLE 5: SCREENING FOR SPECIFIC B-CELLS USING FLUORESCENCE ACTIVATED CELL SORTING (FACS)

B-cells isolated as described in Example 1 above may be screened for their specificities as described in Casali, P. et al. (op. cit.). Approximately $1 \times 10^6$ B-cells will be incubated for 35 minutes in ice-chilled sterile Hanks balanced salt solution without $Ca^{2+}$ or $Mg^{2+}$ and without phenol red containing 1% bovine serum albumin (BSA-HBSS) and appropriate amounts of biotinylated antigen. Typically, 1 mg/ml antigen will be incubated in 0.1M sodium bicarbonate (pH 8.8) and 10% dimethylsulfoxide (DMSO) in the presence of 1 nanogram of d-biotin-N-hydroxysuccinimide ester for 2 hours at room temperature. The cells may be washed with cold BSA-HBSS and then allowed to react with FITC (fluorescein isothiocyanate) avidin (FITC-avidin) $(1.56 \times 10^{-7}M)$ in cold BSA-HBSS for 45 minutes. A small sample of B-cells ($10^6$) will be simultaneously incubated with BSA-HBSS devoid of biotinylated antigen and allowed to react with FITC-avidin under similar conditions. After further washing with cold BSA-HBSS, cells from both samples will be resuspended at a density of $10^6$ cells per ml in the same medium and at different times applied to a Becton and Dickinson Model 440 FCS with a 488 Argon laser (Becton and Dickinson, Mountain View, Calif.). Cells which fluoresce in the presence of biotinylated antigen and FITC—avidin are identified and isolated.

EXAMPLE 6: USE OF RAS TRANSFORMED, FULLY DIFFERENTIATED LCL FOR FUSION PARTNERS

Normal human B-cells will be isolated as in Example 1 above, immortalized with EBV as in Example 2 above and transformed with a retroviral vector having an activated ras gene as in Example 4. Successful transformants will be selected by their resistance to G418. Fully differentiated, G418 resistant transformants will be isolated as in Example 4 above.

The fully differentiated, ras-transformed LCL will be selected for growth in appropriate selective media (e.g. containing 6-thioguanosine). LCL that are resistant to growth in this media can be selected for growth in HAT medium because they lack a functional gene for HGPRT.

IgG secreting normal human B-cells, secreting antibodies directed against a specific antigen (e.g. HIV gp41), will be isolated as described in Example 5 above from an HIV seropositive patient. These B-cells will be fused with the mutagenized, immortalized fully differentiated ras-transformed LCL described above using techniques well-known in the art. The HAT resistant (HGPRT minus) cells will be used as fusion partners as described below.

The fusions will be preferably performed in the presence of 50% (w/v) propylene glycol (m.w. 1500, Sigma Chemical, St. Louis, Mo.). After fusion, the cells will be resuspended in culture medium supplemented with 10% fetal bovine serum and plated overnight in 6 well tissue culture plates. The next day, cells are washed once and plated into 96 well flat bottomed microplates.

Successful fusions will be screened for resistance to G418 and growth in HAT medium. Hybridoma secreting IgG directed against HIV gp41 will be identified and isolated as in Example 5 above.

The present invention has been illustrated in the foregoing examples. As those skilled in the art will appreciate, however, the present invention is not limited to these specific examples, but is receptive of many additions, deletions and substitutions without departure from the spirit of the invention and/or the scope of the following claims.

What is claimed is:

1. A method for preparing differentiated, transformed human B-cells that can secrete monoclonal antibodies and grow in vitro, which comprises the steps of:
    infecting human B-cells that express antibodies of a desired specificity with Epstein-Barr Virus,
    transfecting said Epstein-Barr Virus-infected human B-cells with a vector containing, an activated ras gene conferring on said cells the ability to differentiate, and
    selecting infected differentiated transformants secreting said antibody.

2. The method of claim 1 wherein said gene also confers on said cells the ability to grow on semi-solid media or in animals and enhances the antibody-producing ability of said cells.

3. The method of claim 1 which comprises transfecting said human cells with an effective amount for transfection of said vector.

4. The method of claim 1 wherein said selecting step comprises selecting for Epstein-Barr Virus infected human B-cells expressing said ras vector.

5. The method of claim 1 wherein said vector comprises a retroviral vector.

6. The method of claim 5 wherein said retroviral vector is a member selected from the group consisting of SVNras and raszip6.

7. A method for obtaining differentiated, transformed human B-cells comprising the steps of:
    infecting human B-lymphocytes with Epstein-Barr Virus,
    transfecting said infected B-lymphocytes with a vector containing an activated ras gene which confers on said cells the ability to differentiate, and
    recovering said infected differentiated transformants.

8. The method of claim 7 wherein said gene also confers on said cells the ability to grow on semi-solid media or in animals.

9. A transformed human cell comprising a human B-lymphocyte infected with Epstein-Barr virus, said cell having been transfected with DNA segments coding for a selectable genetic marker, and an activated ras gene in the proper orientation and correct reading frame.

10. The transformed human cell of claim 9 wherein said human ras gene is mutated at condon 12.

11. The cell of claim 10 secreting human monoclonal antibodies.

12. A transformed human cell comprising a human B-cell infected with Epstein Barr virus and transfected with a vector containing an activated ras gene.

* * * * *